(12) United States Patent
Lopez et al.

(10) Patent No.: US 6,936,280 B1
(45) Date of Patent: Aug. 30, 2005

(54) METHOD FOR PREPARING A COMPOSITION BY EXTRACTION OF MOTHER-OF-PEARL, COMPOSITION OBTAINED BY SAID METHOD AND USE THEREOF IN COSMETICS AND DERMATOLOGY

(75) Inventors: Evelyne Lopez, Paris (FR); Alfred Edouard Chemouni, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 80 days.

(21) Appl. No.: 10/089,982

(22) PCT Filed: Oct. 5, 2000

(86) PCT No.: PCT/FR00/02766

§ 371 (c)(1),
(2), (4) Date: Apr. 3, 2002

(87) PCT Pub. No.: WO01/24804

PCT Pub. Date: Apr. 12, 2001

(30) Foreign Application Priority Data

Oct. 5, 1999 (FR) .............................. 99 12409

(51) Int. Cl.$^7$ .......................... A61K 31/74; A61K 9/14; A61K 35/56; A61K 47/00; A01N 25/00
(52) U.S. Cl. .................... 424/547; 424/489; 424/78.03; 514/773; 514/951
(58) Field of Search ................................ 424/547, 489, 424/78.03, 78.05, 520; 514/951, 773

(56) References Cited

FOREIGN PATENT DOCUMENTS

JP          10236941 A  *  9/1998  ............ A61K/7/48

OTHER PUBLICATIONS

Lopez et al Tissue & Cell (1992), 24(5): 667–679. Demonstration of the capacity of nacre to induce bone formation by human osteoblasts maintained in vitro.*

Silve et al. Calcified Tissue International (1992), 51(5): 636–369. Nacre initiates biomineralization by human osteoblasts maintained in vitro.*

* cited by examiner

*Primary Examiner*—Michele Flood
(74) *Attorney, Agent, or Firm*—Blakely Sokoloff Taylor & Zafman

(57) ABSTRACT

A method for preparing a composition, comprising a) reducing mother-of-pearl into powder with grain size distribution ranging between about 1 and about 300 μm; b) placing the obtained powder in close contact with an extracting agent in the form of a hydroglycol solution of at least a collagen, of at least a proteoglycan or a mixture thereof; then c) in collecting the extraction mixture, formed by the close contact, constituting the desired composition. The composition obtainable by said method has very interesting properties relative to the skin and/or skin appendages, in particular tissue-regenerating properties, enabling for instance improved wound healing, and anti-ageing properties for preventing and/or visibly reducing effects related to skin and/or skin appendage ageing.

26 Claims, 15 Drawing Sheets

* The 110 kDa and 140 kDa marks are calculated from the equation rf=f (logMW)

* The 110 kDa and 140 kDa marks are calculated from the equation rf=f (logMW)

1: Biochemical detection of alkaline phosphatase activity
2: Immunochemical detection of the pressure of alkaline phosphatase

METHOD FOR PREPARING A COMPOSITION BY EXTRACTION OF MOTHER-OF-PEARL, COMPOSITION OBTAINED BY SAID METHOD AND USE THEREOF IN COSMETICS AND DERMATOLOGY

SUMMARY OF THE INVENTION

The present invention relates to a method for preparing a composition comprising all the components of mother-of-pearl, at least one collagen and at least one proteoglycan, to the composition which can be obtained using this method and to the use of the latter both in the pharmaceutical domain and in the domain of cosmetics, in particular for combating the effects of aging of the skin and/or of superficial skin growths.

BACKGROUND OF THE INVENTION

Mammals are protected from the outside environment by a barrier consisting of the skin, which is a highly structured tissue composed of several layers, but sensitive to attacks due to the variations in the extracorporeal environment. This situation is unique in the animal kingdom since fish and frogs secrete mucus, birds are covered with feathers, and submammalian and mammalian vertebrates, except current Hominidae, are covered with hair.

Humans have lost these protective attributes: they have a skin which must be protected and which can be stimulated in order to help it to combat attacks and aging.

In particular, it is known that aging is a physiological phenomenon which results in particular in thinning of the skin and a loss of elasticity, leading in particular to the appearance of more or less deep wrinkles. Loosening or drying-out of the surface and anarchic pigmentation may also be observed.

The skin comprises three layers: the epidermis, the dermis and, deep down, the hypodermis.

The outermost protective envelope of the skin, the epidermis, which tightly covers the dermis, consists, at the surface, of the stratum corneum. The stratum corneum is made of two layers: the stratum disjunctum at the surface, the particularity of which is desquamation, and the stratum compactum, the deepest, which plays the role of a barrier. The epidermis, which is easy to observe macroscopically since it is at the surface, has been the subject of many studies. Known responses are those caused by certain agents of the extracorporeal environment or those resulting from the application of active substances of diverse origins. The cells of the epidermis result from the activity of the cells of the basal layer which lies on a basal membrane separating the epidermis from the dermis.

The dermis results from the biosynthetic activity of fibroblasts, which produce the constituents of the extracellular matrix. The latter is made up of four major families of macromolecules: collagens, elastin, structural glycoproteins and proteoglycans. The dermis has the ability to respond to the signals given out by the epidermis, which, in response, also sends signals to the epidermis. In general, exchanges exist between these various dermal and epidermal layers of the skin, which are intended to ensure cell renewal and the cohesion and moisturization of the outer layers.

Many active agents have been proposed for preventing or delaying the effects of aging.

Among these, mother-of-pearl has been used since the beginning of time in aesthetics and in conventional pharmacopeiae. Moreover, mother-of-pearl is known for its bone-regenerating properties.

It is in particular known that mother-of-pearl, or conchiferous aragonite, is a biogenic mineralized formation; it consists of an organic matrix of fibrous and nonfibrous substances representing approximately 1.7 to 2% of the total mass (Taylor et al, Bulletin of the British Museum (Natural history) Zoology. Suppl. 3125 pp.+29 Plates, 1969) and of calcium carbonate crystallized in orthorhombic form, named aragonite, combined with trace elements (sodium, magnesium, lanthanum, zinc, bromine, cesium, iron, manganese, chlorine, copper, potassium, calcium, strontium and sulfur). More particularly, the entire organic phase of mother-of-pearl is in the form of an organic matrix composed of fibrous proteins, consisting in particular of ancestral collagens lacking hydroxyproline and hydroxylysine, and of nonfibrous proteins. Approximately 50% of the organic matrix of mother-of-pearl is water-soluble. The remaining 50% can only be obtained after decalcification.

However, the products of the prior art, obtained by mixing a mother-of-pearl powder with a pulverulent, inert diluent or excipient, as described, for example, in application WO 97/23231, cause undesirable phenomena of skin irritation, due to the presence of the mother-of-pearl in the form of powder (in particular of its major component, aragonite or $CaCO_3$). It is therefore imperative that the content of mother-of-pearl powder in these products should be very limited in order to avoid these irritation phenomena. These undesirable phenomena of irritation are in particular caused by the pH, which is too basic, of these known products, in contact with the skin. In addition, the known products based on mother-of-pearl powder have specific formulation problems, in particular stability (breaking of emulsions) and of adjustment of the pH to a less basic value.

Moreover, application WO 97/24133 describes a method for preparing biologically active substances from mother-of-pearl, by bringing a mother-of-pearl powder into contact with an aqueous solvent chosen from pure, double-distilled or apyrogenic water, optionally supplemented with salts, from which the water-soluble fraction is then separated so as to recover only the aqueous fraction, therefore essentially lacking the water-insoluble organic phase and inorganic components of mother-of-pearl. This method cannot therefore enable, in particular, the preparation of a composition comprising in particular all of the components of mother-of-pearl, particularly the entire organic phase of mother-of-pearl.

DETAILED DESCRIPTION OF THE INVENTION

It has now been noted, quite surprisingly and unexpectedly, that the implementation of a specific method makes it possible to obtain a novel composition comprising not only all of the components of mother-of-pearl, but also an advantageous combination of the latter with certain compounds which make it possible at least to potentiate the activity of the components of mother-of-pearl, or even to provide a synergistic effect, for the purpose in particular of preventing and/or visibly decreasing the effects relating to aging of the skin and/or superficial body growths.

A subject of the present invention is thus a method for preparing a composition, characterized in that it comprises the steps consisting:

a) in reducing mother-of-pearl to a powder with a particle size of between approximately 1 and approximately 300 $\mu$m;

b) in bringing the mother-of-pearl powder thus obtained into close contact with an extracting agent in the form of an aqueous-glycolic solution of at least one collagen, or of at least one proteoglycan or of a mixture thereof; and then c) in recovering the extraction mixture formed as a result of the bringing into close contact, constituting the desired composition.

The present method makes it possible to obtain a composition in the form of the extraction mixture obtained in step b).

The mother-of-pearl used for the implementation of the method according to the invention may be obtained from shells of nacreous mollusks and of some cephalopods, for example nautilus). In particular, it is obtained from oysters, such as *Pinctada maxima*.

Raw mother-of-pearl is used, which is free of other polysaccharide- and calcite-rich shell elements. The starting material is preferably white mother-of-pearl, otherwise it is necessary to provide a step for removing the pigments which may cause intolerance.

This is a readily available raw material, the use of which does not impact negatively on natural populations. In fact, most of these oysters or other nacreous mollusks are farmed.

Furthermore, an additional advantage comes from the fact that the raw material can be obtained from oyster shells which have produced pearls; specifically, a pearl oyster is removed from the productive pool after having produced at most three pearls in succession, although it has a thick layer of mother-of-pearl of excellent quality (grade A). The present invention therefore provides an extra opportunity for using mother-of-pearl downstream of pearl farming.

The particle size of the mother-of-pearl powder used for carrying out the present method is between approximately 1 and approximately 300 $\mu$m, as measured with conventional means within the scope of those skilled in the art, such as the sieving technique and/or the LASER-reading technique.

According to a particular embodiment of the method according to the invention, the mother-of-pearl is reduced to a powder with a particle size of between approximately 50 and approximately 100 $\mu$m.

According to another particular embodiment, the mother-of-pearl is reduced to a powder with a particle size of between approximately 15 and approximately 50 $\mu$m, which makes it possible to improve the yield by approaching the size of a crystalline unit (for example, the elemental unit of mother-of-pearl from *Pinctada maxima* is the biocrystal, a very voluminous hexagonal crystal of aragonite of 9 to 12 $\mu$m).

The following procedure is in particular carried out in order to reduce the mother-of-pearl to powder according to step a) of the present method.

In a first phase, the outer part of the shell (periostracum) is removed from the raw mother-of-pearl by grinding or any other nondenaturing method.

The sheets of mother-of-pearl are then reduced to fragments by crushing so as to then be able to perform micronization. The fragments intended to be micronized are preferably between approximately 2 and approximately 5 centimeters in length and are approximately 0.3 centimeters thick.

In a second phase, the fragments are micronized.

The mother-of-pearl can be used without prior decontamination. In the case of prior decontamination, a very rapid decontaminating wash is performed, without soaking the fragments, in a solution of sodium hypochlorite at 6.6% of active chlorine (12°). Drying must be carried out extemporaneously so as to remove all traces of water.

The grinding must be done dry in zirconium jars reserved exclusively for this purpose, washed (water containing bleach, rinse, then wash with distilled water) and hot-sterilized beforehand. The crushing is carried out with zirconium balls, themselves sterilized.

The raw mother-of-pearl reduced to powder can be sterilized in two different ways:

sterilization by irradiation with $\gamma$-rays, 2.5 Mrad;

hot-sterilization for 1 to 2 hours in an autoclave at 100° C. The mother-of-pearl is degraded (inorganic matrix and organic matrix) only from approximately 250° C. (Balmain, Hannoyer and Lopez, "Fourier transform infrared spectroscopy (FTIR) and X-ray diffraction analyses of mineral and organic matrix during heating of Mother of Pearl (nacre) from the shell of the mollusc *Pinctada Maxima*", J. Biomed. Mater. Res. (Appl. Biomater.), vol. 48(5): 749–754, 1999). This sterilization does not therefore destroy its various components.

Step b) of the method according to the invention consists in bringing the mother-of-pearl powder described above into close contact with an extracting agent in the form of an aqueous-glycolic solution of at least one collagen, of at least one proteoglycan or of a mixture thereof.

According to the invention, the term "aqueous-glycolic solution" is intended to mean a solution of the collagen and the proteoglycan obtained using an aqueous-glycolic solvent, i.e., in general, a solvent in the form of a mixture of water and at least one glycol.

The term "glycol" is intended to mean, in a known manner, any compound having two alcohol functions. In particular, the glycol which may be used is chosen from the group consisting of ethylene glycol, propylene glycol, butylene glycol and mixtures thereof.

The water which may be used to form the aqueous-glycolic solvent may be pure, double-distilled, apyrogenic or demineralized water, or else deionized water.

The water:glycol weight ratio in the aqueous-glycolic solvent is preferably between approximately 1:100 and approximately 100:1, and more particularly between approximately 1:1 and approximately 20:1.

The extracting agent is preferably an aqueous-glycolic solution of at least one collagen.

The collagen which may be used in aqueous-glycolic solution in the extracting agent according to the invention may be any collagen constituting the intracellular substance of the connective tissue, available in the animal kingdom, known to those skilled in the art.

Most particularly, use is preferably made of a marine collagen, i.e. a collagen derived from an organism of marine origin, such as marine vertebrates. In particular, marine collagen is the main constituent of the connective tissues of fish, in which it fulfills an essential role in the structure of the skin, muscles, tendons and ligaments.

Mention may be made more particularly of the marine collagen "PANCOGENE$^R$ MARIN", as sold by the company Gattefossé (Saint Priest, France), the INCI name of which is "Soluble Collagen" (referencing in Japan: "water soluble collagen"; MHV: 20800CZY00100000). It is a collagen extracted from skins of unprotected species of fish from warm seas, belonging to the class Teleostei.

Mention may also be made of the marine collagen "COLLAGEN NATIF MARIN—Code 690", as marketed by the company Laboratoire Industriel de Biologie (Soisy Sous Montmorency, France), the CTFA name of which is "Amino Collagen Amino Acid". It is a water-soluble acid collagen extracted from fish skins.

Preferably, a collagen concentration is used which is between approximately 0.0001 and approximately 50% by weight, and more particularly between approximately 0.01 and approximately 15% by weight, relative to the total weight of the extracting agent.

The extracting agent is also preferably an aqueous-glycolic solution of at least one proteoglycan.

The proteoglycan which may be used in aqueous-glycolic solution in the extracting agent according to the invention may be any proteoglycan known to those skilled in the art, in particular any proteoglycan not containing sulfur.

In particular, the proteoglycan is chosen from the group consisting of hyaluronic acid, chondroitin sulfate, dermatan sulfate, heparan sulfate, keratan sulfate and mixtures thereof.

Hyaluronic acid is most particularly preferred, such as that marketed by the company Laboratoire Industriel de Biologie (Soisy Sous Montmorency, France).

The proteoglycan concentration used is preferably between approximately 0.0001 and approximately 40% by weight, and more particularly between approximately 0.01 and approximately 10% by weight, relative to the total weight of the extracting agent.

Of course, the extracting agent may also comprise any additional compound known to those skilled in the art, which is suitable f or the extraction step itself or in view of the possible uses of the composition prepared by the present method, such as those described hereafter. The extracting agent may thus, for example, also comprise complexing agents, such as EDTA (ethylenediaminetetraacetic acid).

According to a particularly preferred embodiment of the present invention, the mother-of-pearl powder is brought into close contact with the extracting agent according to step b) by preparing a mixture, consisting of the mother-of-pearl powder and the extracting agent, such that it comprises, relative to its total weight, approximately 20 to approximately 60% by weight of mother-of-pearl powder obtained in step a), as described above, and the remainder as extracting agent as described above.

The mother-of-pearl powder can be brought into close contact with the extracting agent, according to step b) of the present method, in particular by suspending the mother-of-pearl powder in the extracting agent, with vigorous and homogeneous mechanical stirring, so as to allow an extraction coating of the mother-of-pearl particles.

The procedure may, for example, be carried out at ambient temperature, i.e. at a temperature of about 20° C. for approximately 1 hour, but the durations and temperatures may be adjusted, by those skilled in the art, in particular depending on the starting particle size of the mother-of-pearl powder.

According to another embodiment, step b) for bringing about contact may be carried out by passing the extracting agent, under pressure, through the mother-of-pearl powder, which has been immobilized. This immobilization may, for example, be effected using a column, of the HPLC type, optionally in a mixture with fillers which allow better diffusion of the extracting agent and avoid compaction of the mother-of-pearl powder.

Without wishing, however, to be linked to any particular theory, it is thought that the presence of the collagen and of the proteoglycan in the extracting agent, in particular of the marine collagen and of the hyaluronic acid, would promote extraction of related compounds present in the mother-of-pearl, via a physicochemical phenomenon of affinity, with, in addition, potentiation of the effects of the components thus extracted from the mother-of-pearl. In particular, it is thought that extraction of the ancestral collagens from the mother-of-pearl would be promoted by the presence of the marine collagens and extraction of both the adhesion proteins (decorin and cytokines) and the proteoglycans from the mother-of-pearl would be promoted by the presence of the proteoglycan chosen.

Be that as it may, the close contact is preferably brought about, for a given temperature, for a period of time sufficient to produce a virtually complete extraction. According to the invention, the term "virtually complete extraction" is intended to mean the extraction of all the extractable components from the mother-of-pearl when it is brought into contact with the extracting agent.

In other words, the production of an equilibrium for the total concentrations in particular of collagens or of proteoglycans in the aqueous-glycolic liquid phase corresponds to achieving said "virtually complete extraction".

It is therefore within the scope of those skilled in the art to determine the "virtually complete" nature of such extraction, for example by regularly measuring these total collagen or proteoglycan concentrations in the aqueous-glycolic liquid phase.

Be that as it may, the step for bringing about contact may comprise, before it ends, a period during which the suspension of the mother-of-pearl powder in the extracting agent is left to stand (stirring arrested).

At the end of step b) for bringing about contact, the extraction mixture, formed as a result of the bringing into close contact, which constitutes the desired composition, is recovered.

This composition, in the form of an aqueous-glycolic suspension, may be stored as it is before use. For practical reasons of subsequent implementation (storage, transport, formulation, etc.) it is also possible to separate the liquid phase of this composition from the solid phase.

Thus, according to one variant, the method according to the invention is characterized in that, at the end of step b), the extraction mixture, formed as a result of the bringing into close contact, which constitutes the desired composition, is recovered and the liquid phase of the composition is separated from the solid phase by means known to those skilled in the art, such as ultra-filtration means, tangential filtration means, etc.

It is understood that the solid and liquid phases thus separated, together, constitute the composition prepared as described above. It may thus be envisioned that, in a subsequent formulation using this composition, with pharmaceutically or cosmetically suitable excipients, the composition may be reconstituted at any step of the formulation, by addition of the respective solid and liquid phases, simultaneously or separated over time, for reasons of convenience of formulation. Given the above, it is understood that a subject of the present invention is also the liquid phase as obtained at the end of the separation step described above. Similarly, a subject of the present invention is also the solid phase as obtained at the end of the separation step described above.

A subject of the present invention is also a novel composition which can be obtained using the method as described above (comprising the solid and liquid phases, with or without a separation step as described above).

In particular, this composition is characterized in that it comprises at least, in the form of an aqueous-glycolic suspension of a liquid phase and of a solid phase:

aragonite ($CaCO_3$);

trace elements chosen from the group consisting of sodium, magnesium, lanthanum, zinc, bromine, cesium, iron, manganese, chlorine, copper, potassium, calcium, strontium, sulfur and mixtures thereof;

fibrous proteins from mother-of-pearl, in particular ancestral collagens from mother-of-pearl, related to the marine collagens of the extracting agent (see FIG. 1 described below);

nonfibrous proteins from mother-of-pearl, in particular proteins related to adhesion proteins, such as decorin (see FIG. 2 described below);

at least one collagen not derived from mother-of-pearl and/or at least one proteoglycan not derived from mother-of-pearl.

It is, of course, understood that, according to the invention, the expressions "collagen not derived from mother-of-pearl" and "proteoglycan not derived from mother-of-pearl" are intended to mean, respectively, the collagen and the proteoglycan used for the extracting agent of step b) of the present method. Similarly, the expression "aqueous-glycolic suspension" is explained by the fact that the composition according to the invention comprises not only soluble components (in aqueous-glycolic solution) but also insoluble components (in particular aragonite).

Moreover, the preferences stated above for the method according to the invention apply, of course, to this composition.

Thus, in particular, the collagen not derived from mother-of-pearl in the composition according to the invention is preferably a marine collagen, and more particularly a marine collagen chosen from the group consisting of "PANCOGENE$^R$ MARIN", "COLLAGENE NATIF MARIN—Code 690" and mixtures thereof. Similarly, the proteoglycan not derived from mother-of-pearl may be any proteoglycan known to those skilled in the art, in particular any proteoglycan not containing sulfur, and is in particular chosen from the group consisting of hyaluronic acid, chondroitin sulfate, dermatan sulfate, eparan sulfate, keratan sulfate and mixtures thereof, and is more particularly hyaluronic acid.

As shown in greater detail in the examples below, this composition has properties which are very advantageous with respect to the skin and/or superficial body growths, in particular tissue-regenerating properties, allowing for example improved wound healing, and anti-aging properties making it possible to prevent and/or visibly decrease the effects related to aging of the skin and/or superficial body growths. Its action on the various cell types of the skin is one of repair and of regulation of the physiological balance between its various constituents. More particularly, its organic and inorganic components act in particular, at several levels, on keratinocyte metabolism. This composition allows restructuring of the epidermis, contributing to better protection of the deepest layers. The epidermis becomes more resistant and deeper and interacts continually with the dermis. In addition, this composition allows enrichment in elastin and collagens. The skin is more elastic and firmer. It is resistant and its components are renewed at a sustained rhythm. In addition, this composition stabilizes synthesis of pigments and promotes microcirculation. Finally, this composition has the advantage of being totally innocuous and that of having an anti-inflammatory, and therefore soothing, effect.

Thus, a subject of the present invention is also a pharmaceutical composition, characterized in that it comprises, as active principle, the novel composition as described above, which can be obtained using the method according to the invention, and a pharmaceutically acceptable excipient.

The pharmaceutically acceptable excipient is preferably an excipient suitable for dermatological application.

A subject of the present invention is also the use of this novel composition as described above, which can be obtained using the method as described above, for producing a medicinal product intended for the treatment of tissue regeneration disorders of the skin and/or superficial body growths.

Moreover, a subject of the present invention is the use of the novel composition as described above, which can be obtained using the method as described above, for producing a medicinal product intended for the treat-ment of disorders of the skin and/or superficial body growths related to aging.

Finally, a subject of the present invention is the use of the novel composition as described above, which can be obtained using the method as described above, for producing a medicinal product intended for the treat-ment of inflammatory skin manifestations.

A subject of the present invention is also a cosmetic composition, characterized in that it comprises, as cosmetically active principle, the novel composition as described above, which can be obtained using the method according to the invention, and a cosmetically acceptable excipient.

Any cosmetic excipient known to those skilled in the art may be used.

Of course, the cosmetic composition according to the invention may also contain ingredients of the cosmetic type, known to those skilled in the art, such as moisturizers, softeners, or chemical or organic screening agents.

The pharmaceutical and cosmetic compositions described above may, in particular, be in the form of a cream, an ointment, a gel, a lotion, an oil-in-water emulsion or a water-in-oil emulsion, or may be combined with any pharmaceutically or cosmetically acceptable vector, such as liposomes.

In addition, a subject of the present invention is the use of the novel composition as described above, which can be obtained using the method according to the invention, for producing a cosmetic composition intended for cosmetic treatment for tissue regeneration of the skin and/or superficial body growths.

Moreover, a subject of the present invention is the use of the novel composition as described above, which can be obtained using the method according to the invention, for producing a cosmetic composition intended for the cosmetic treatment of modifications related to aging of the skin and/or superficial body growths.

Finally, a subject of the present invention is a method of cosmetic treatment for tissue regeneration of the skin and/or superficial body growths, characterized in that the novel composition as described above, which can be obtained using the method according to the invention, is applied to the skin and/or superficial body growths.

Furthermore, a subject of the present invention is a method of cosmetic treatment of modifications related to aging of the skin and/or superficial body growths, characterized in that the novel composition as described above, which can be obtained using the method according to the invention, is applied to the skin and/or superficial body growths.

Figure 20:
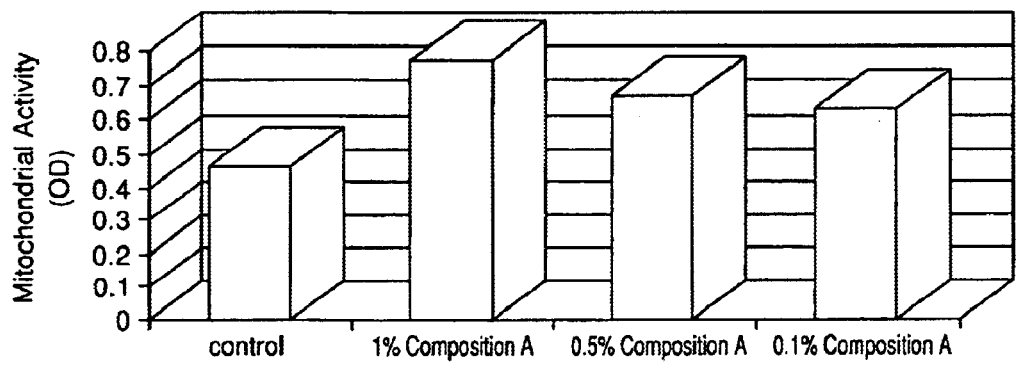

Finally, FIG. 20 is a histogram illustrating the study of the noncytotoxicity of the composition prepared according to the invention.

The following examples are intended to illustrate the present invention but should in no way be interpreted as possibly restricting the scope thereof.

EXAMPLE 1

Method for Preparing a Composition According to the Invention

The material used should be a material of the type under vacuum, completely airtight, and preferably made of stainless steel. It should be washed and rinsed cleanly beforehand so as to avoid any risk of bacterial contamination.

1.1) Mother-of-pearl from *Pinctada maxima*, from which the outer part of the shell (periostracum) has already been removed, and which has already been made into irregular fragments, is used (supplied by the company Pharma Futura 10, rue de Charonne, 75012 PARIS). The size of the fragments is between 2 and 5 centimeters in length and 0.3 centimeters in thickness.

The fragments are given a very rapid decontaminating wash, without soaking, in a solution of sodium hypochlorite at 6.6% of active chlorine (12°) and are then dried extemporaneously in order to remove any trace of water.

The grinding for the micronization must be carried out dry in zirconium jars reserved exclusively for this purpose, washed (water containing bleach+rinse+distilled water wash) and hot-sterilized beforehand. The grinding is carried out using zirconium balls, which are themselves sterilized.

The micronized mother-of-pearl powder thus obtained has a particle size of between 50 and 150 $\mu$m. It is then sterilized by irradiation with $\gamma$-rays, 2.5 Mrad.

The micronized mother-of-pearl powder thus prepared has the following characteristics:

| | |
|---|---|
| appearance | pulverulent |
| color | white |
| odor | characteristic of mother-of-pearl |
| arsenic | < 1 ppm |
| heavy metals | < 10 ppm. |

Bacteriological Analysis:

| | |
|---|---|
| number of aerobic microorganisms | 1550/g |
| degree of hygrometry | 0.3% |

1.2) The following mixture is prepared: 400 grams of *Pinctada Maxima* mother-of-pearl powder micronized as described above (particle size between 50 and 150 $\mu$m) are gradually added to 600 ml of an extracting agent in the form of an aqueous-glycolic solution (water and ethylene glycol, respectively, in a 10:1 weight ratio) comprising 0.18% by weight of the marine collagen "PANCOGENE$^R$ MARIN" (marketed by the company Gattefossé; Saint Priest, France;

INCI name "Soluble Collagen"; referencing in Japan: "water soluble collagen"; MHV: 20800CZY0010000) and 0.2% by weight of hyaluronic acid (marketed by the company Laboratoire Industriel de Bioiogie; Soisy Sous Montmorency, France), relative to the total weight of the extracting agent, with stirring at approximately 4 000 rpm and at a temperature of approximately 20° C. Once this has been added, the stirring and temperature are maintained for 60 minutes. The stirring must be vigorous and homogeneous in order to bring all the particles of the mixture into contact and allow an extraction coating.

The mixture is then left to stand for 6 hours.

The composition thus obtained is composed of an off-white particulate solid phase, in suspension in a liquid phase and at a pH of approximately 8.

This composition comprises:

aragonite ($CaCO_3$);

marine trace elements: sodium, magnesium, lanthanum, zinc, bromine, cesium, iron, manganese, chlorine, copper, potassium, calcium, strontium and sulfur (see table 1 below);

fibrous proteins: various types of protein related to marine collagens, which may be considered to be ancestral collagens from the mother-of-pearl, and the marine collagen "PANCOGENE$^R$ MARIN";

nonfibrous proteins: proteoglycans, including the hyaluronic acid from the mother-of-pearl and the extracting agent, and also adhesion proteins from the mother-of-pearl (decorin rp and cytokine rp; "rp meaning "related peptides or proteins" i.e. peptides or proteins related, respectively, to decorin and to cytokine insofar as they are recognized by the antibodies against the latter molecules).

The technique used to identify the peptides and proteins in the context of the present invention are those described in the following articles:

electrophoresis—SDS-Page method: Laenli method, Nature 1970, 227 680–682;

immunotransfer: Western blot according to Towbin H. et al., 1979, Proc. Natl. Acad. Sci. USA 76(9): 4350–4354 and Burnette W. N. 1981, Analytical Biochemistry 112: 195–203.

Figure 1:
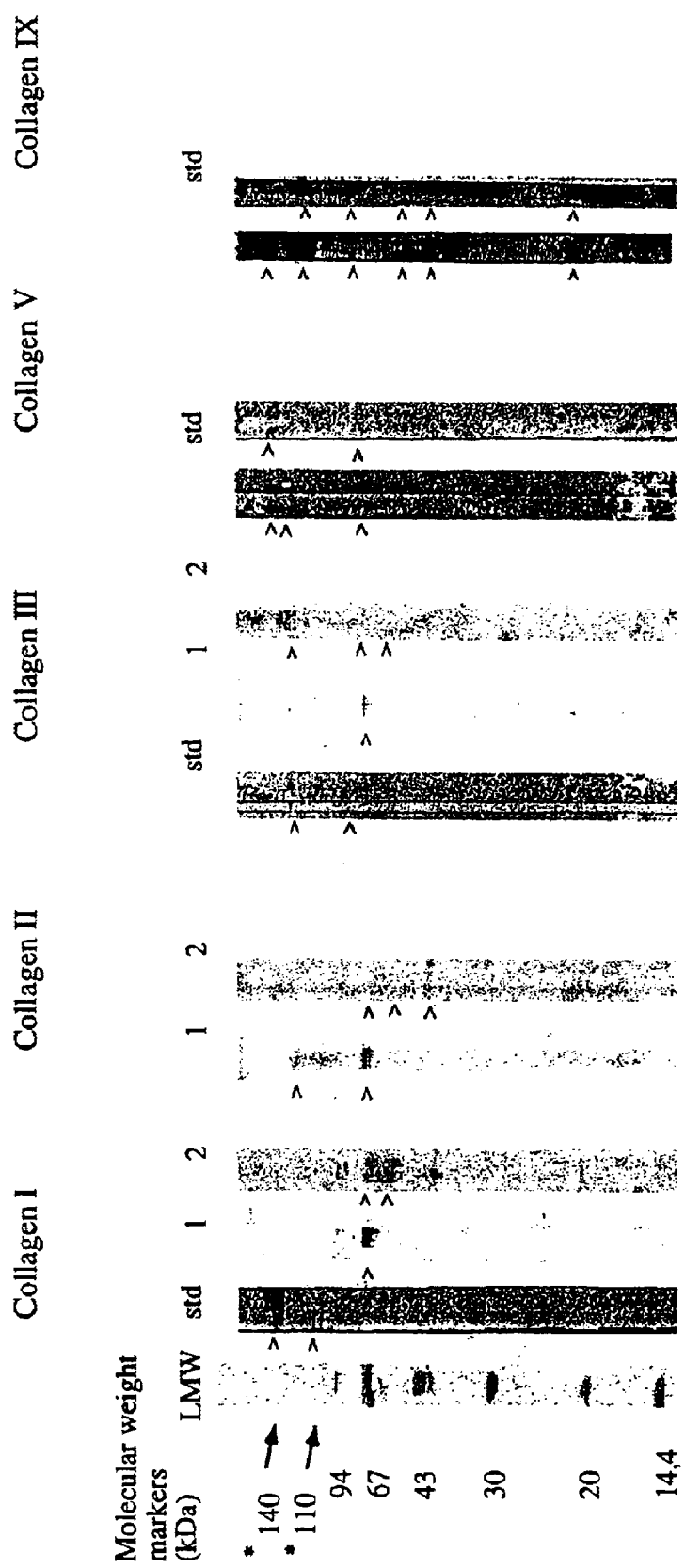
FIGS. 1 and 2 represent a Western blot of a composition prepared using the method according to the invention.
Figure 2:
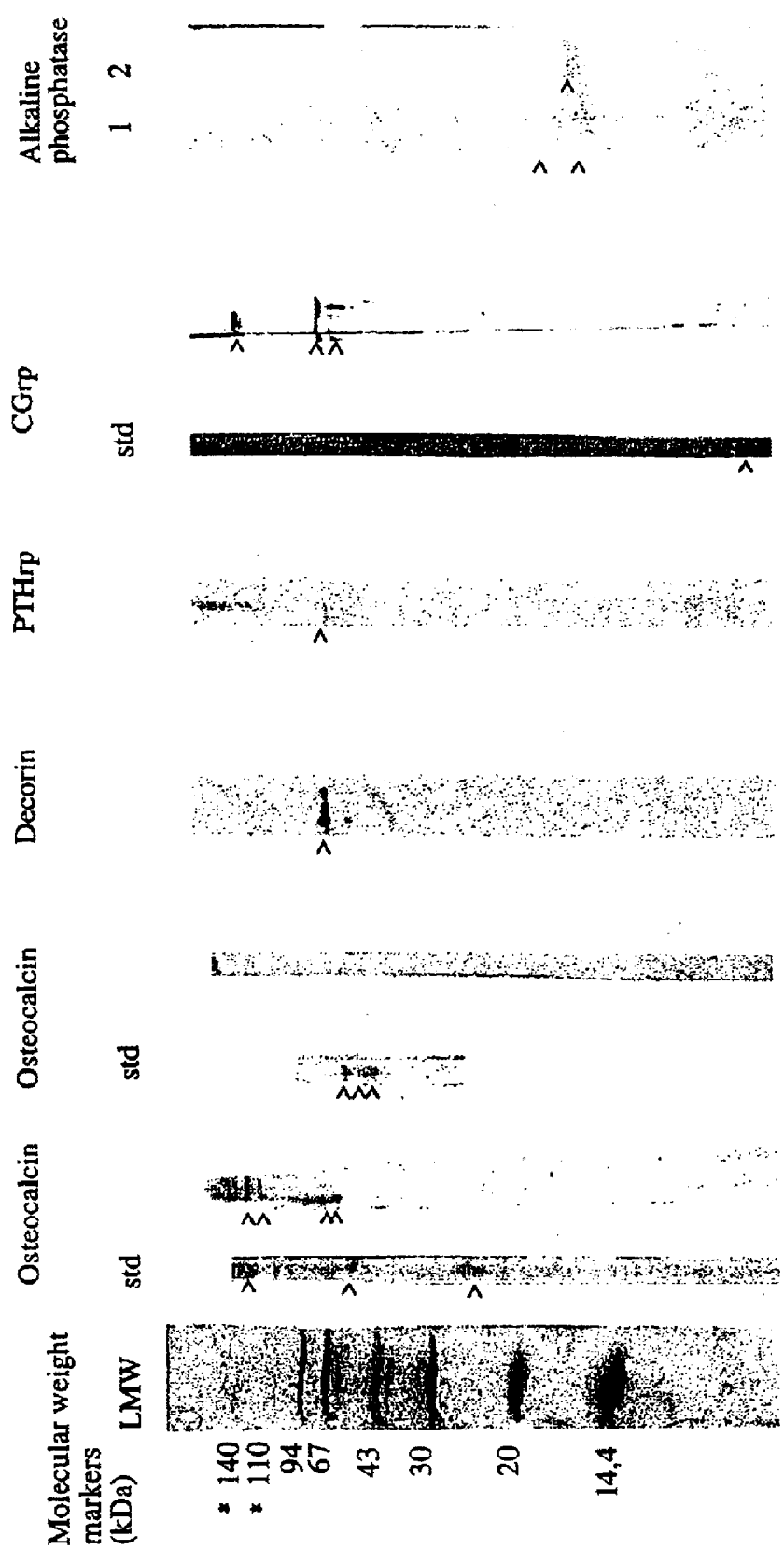

The corresponding Western blots are represented in FIGS. 1 and 2.

Figure 3:
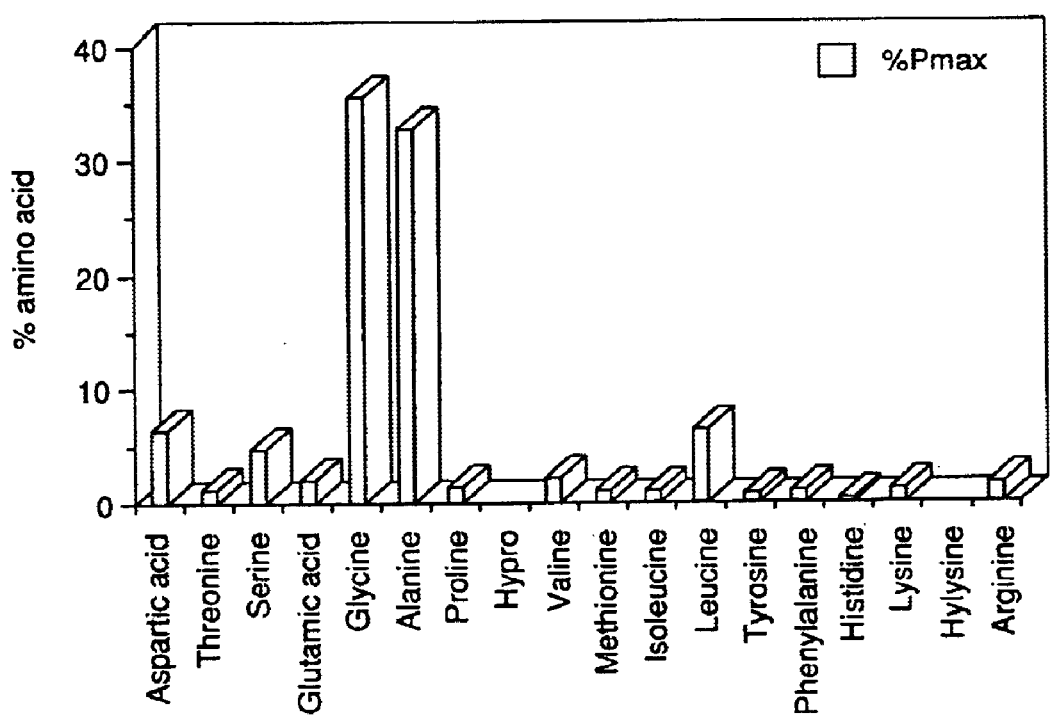
FIG. 3 represents a histogram of the overall amino acid composition of the protein phase of the composition prepared using the method according to the invention.

The amino acid analysis of the protein phase indicates the presence of aspartic acid, threonine, serine, glutamic acid, glycine, alanine, proline, valine, methionine, isoleucine, leucine, tyrosine, phenylalanine, histidine, lysine and arginine. FIG. 3 represents a histogram of the overall amino acid composition.

The composition obtained as described above will be named hereafter "composition A".

TABLE 1 quantitative analysis of the trace elements contained in composition A

| Element | Mean concentration (μg/g) | Element | Mean concentration (g/100 g) |
|---|---|---|---|
| Sulfur | 0.02 | Calcium | 38.8 |
| Magnesium | 2 | | |
| Lanthanum | 0.28 | | |
| Zinc | 0.4 | | |
| Bromine | 1.78 | | |
| Cesium | 5.5 | | |
| Iron | 13.6 | | |
| Manganese | 50 | | |
| Chlorine | 296 | | |
| Copper | 143 | | |
| Potassium | 582 | | |
| Strontium | 1000 | | |
| Sodium | 5420 | | |

EXAMPLE 2

Study of the Activity of Composition A

Histological and cytological scientific research, which uses either in vivo animal models or human cell cultures by exploiting microscopy and the most modern techniques for detecting substances by immunology and immunocytochemistry, currently allows studies to be carried out on a cellular scale, and such a study was performed in order to investigate the active substances of this composition A.

This study essentially concerned three types of cell insofar as they are known to play a major role in the structure, functioning and pigmentation of skin tissue: keratinocytes, fibroblasts and melanocytes. Both the keratinocyte and fibroblast cell types have receptors specific for the active substances of composition A, and in particular of all of the components of the mother-of-pearl which are present therein, leading to a cascade of messages which may reach the level of the deepest layers of the dermis.

The study related not only to their morphological appearance but also to the behavior of their main components, nuclei and cytoplasm, reflecting their synthetic activity and their capacity for renewal. The presence of certain active substance and that of secreted structural proteins was also identified.

1.1) Activity of Composition A on Keratinocytes: Cytokeratin Synthesis by Human Keratinocytes Cultured in the Presence of Composition A 1.1.1) Method Keratinocytes are the outermost cells of our body. They constitute our first protective barrier. Keratinocytes intervene by acting passively and actively. They produce the passive protection by constituting a barrier which plays the role of a shield. This shield is made from cells which are dried-out and anucleated. The strong cohesion of the cells makes it possible to provide a very homogeneous system. Keratinocytes synthesize substances, cytokeratins, which they maintain in their cytoplasm in order to give this barrier structure. The cytokeratins constitute the internal skeleton of keratinocytes. This internal skeleton gives these cells their volume and increases their capacity for intercellular communication and facilitates melanin uptake. The richer the epidermis is in cytokeratins, the more effective it is and the more it gives the skin its young appearance. By facilitating contact between the cells, the cytokeratins prevent loss of the NMS (Natural Moisturizing Factors, such as ceramides, cholesterol or fatty acids).

The active protection of the skin is related to the fact that keratinocytes are the first cells of our body to be in contact with the outside. They have therefore developed a panoply of components intended to inform our body of possible changes in the conditions of our environment. To do this, these cells are capable of synthesizing growth factors intended to stimulate the cells subjacent to the dermis (fibroblasts), in particular PTH related peptide (PTHrp), which is synthesized mainly by keratinocytes and known to be a cellular differentiation factor.

The method used was as follows. It includes a rapid semiquantitative technique which makes it possible to assess the level of each of the secreted proteins present in the cell cytoplasm.

$4\times10^4$ cells are seeded per 0.9 cm$^2$ chamber (8-chamber slides, NUNC) and cultured overnight. After rinsing with HBSS buffer, the medium containing 1% of composition A or the control medium (containing 0% of composition A) is added (450 µl per chamber).

The cultures are incubated for 48 h. After the supernatants have been removed and the Cultures rinsed, the cells are fixed with paraformaldehyde for 30 min at 40° and then rinsed with PBS buffer.

200 µl of anti-cytokeratin primary antibodies are added. The incubation lasts 30 minutes at room temperature. The supernatants are then removed and the cells are rinsed with PBS.

200 µl of secondary antibodies which recognize the primary antibody and are coupled to a fluorescent marker, in this instance fluorescein, are added. After incubation for 30 minutes at room temperature, the supernatants are removed and the cells are rinsed with PBS. The slides are then mounted, followed by examination under an inverted fluorescence microscope (detection of intracytoplasmic cytokeratins by immunofluorescence).

The amount of proteins, in this instance of cytokeratins, synthesized by the cells and thus labeled is proportional to the strength of the fluorescence resulting from the immunolabeling.

1.1.2) Results

Figure 4:
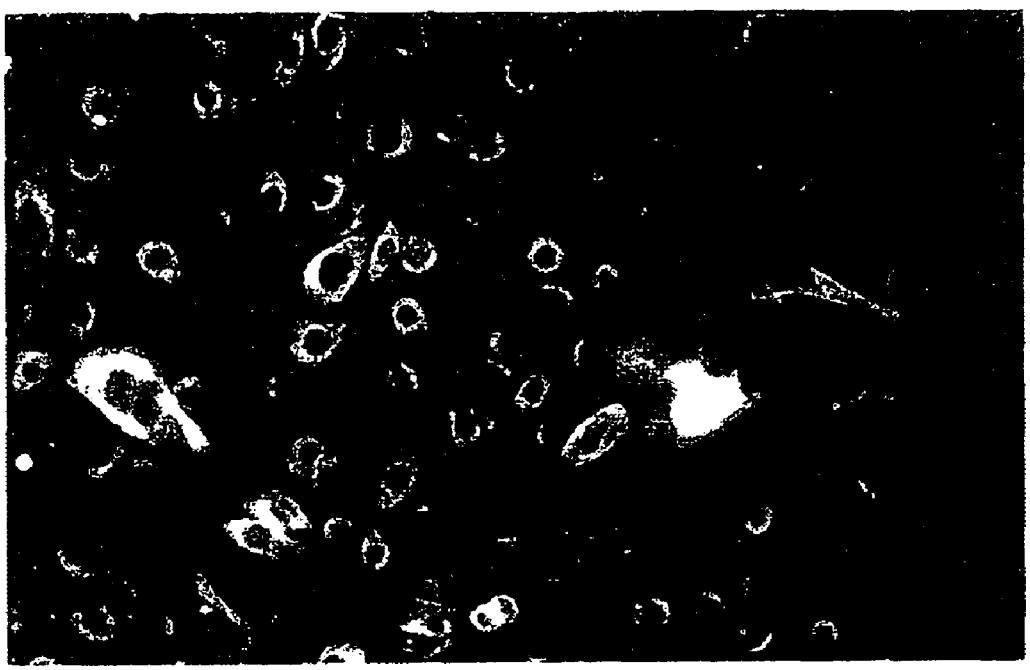
FIGS. 4 and 5 are photographs illustrating the effect of the composition prepared according to the invention on cytokeratin synthesis by human keratinocytes.
Figure 4:
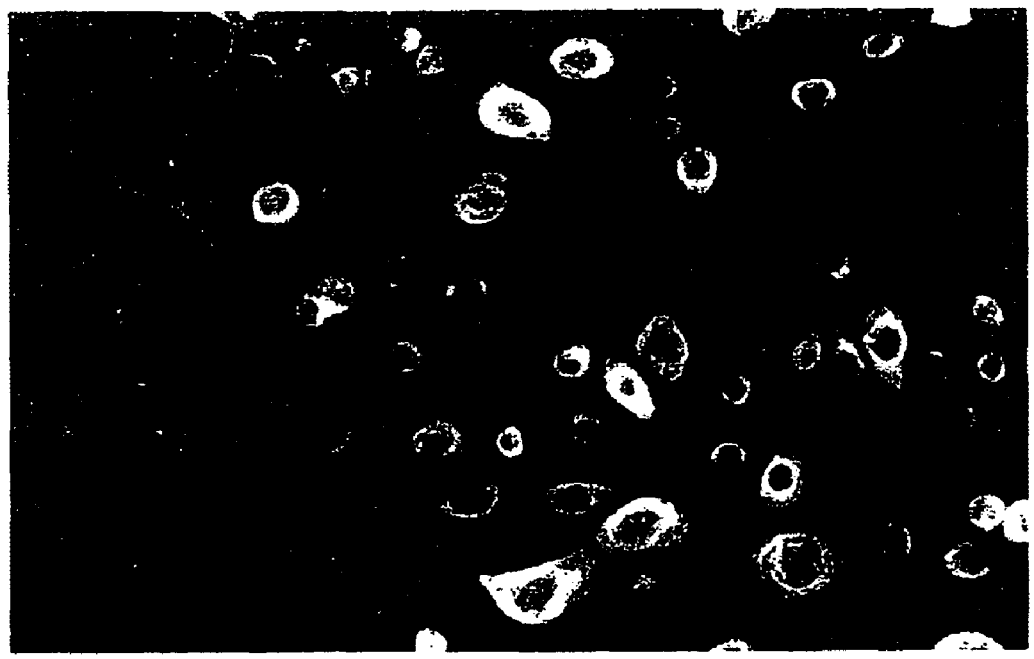
Figure 5:
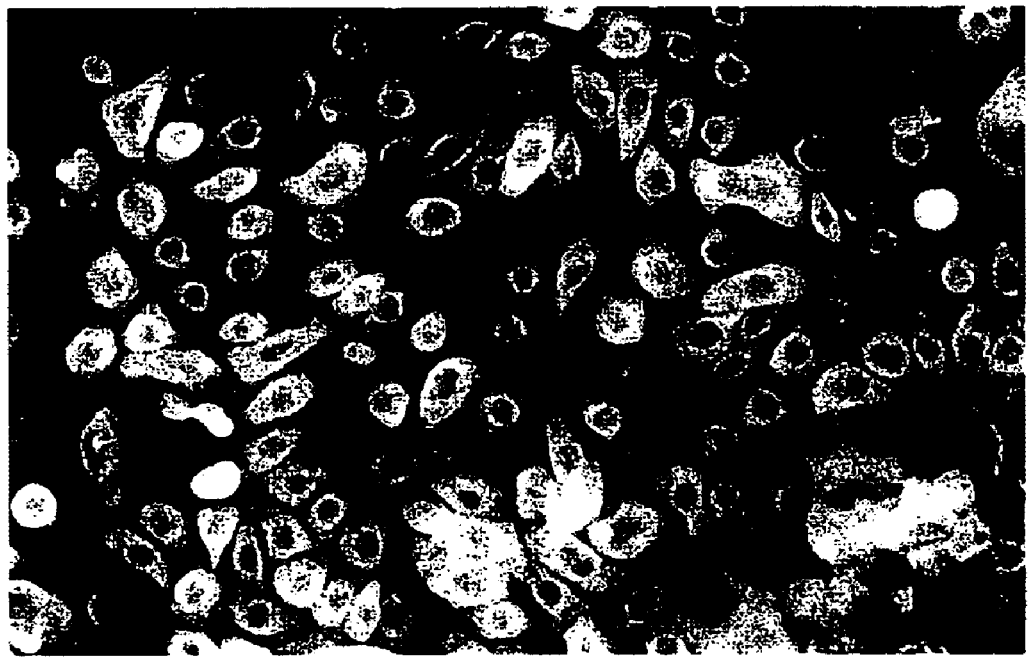
Figure 5:
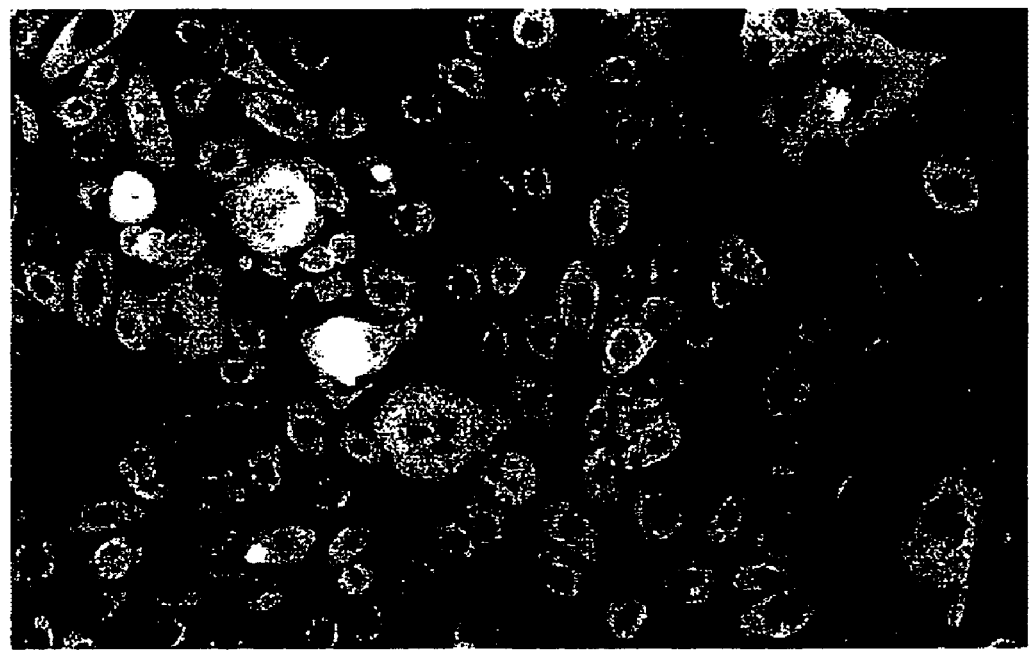
Figure 6:
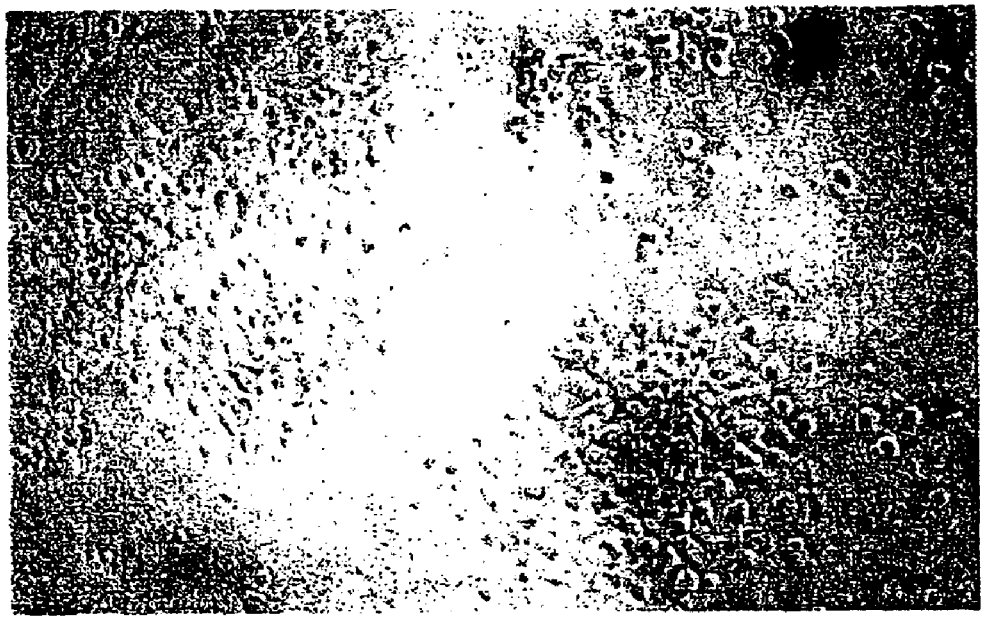
FIGS. 6 and 7 are photographs illustrating the effect of the composition prepared according to the invention on human keratinocytes in culture subjected to estradiol withdrawal.
Figure 7:
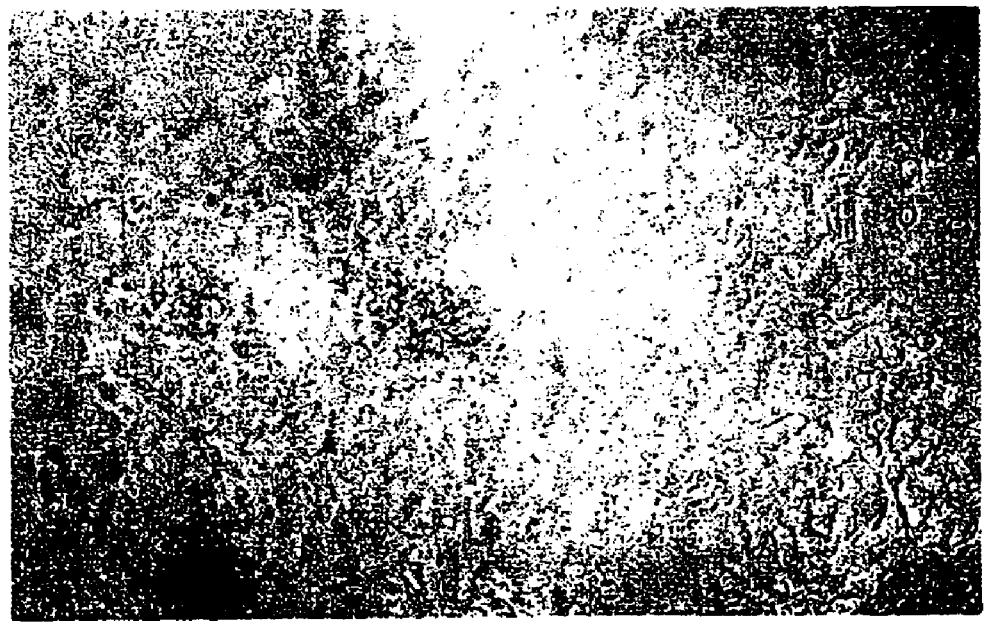

As shown in FIGS. 4 and 5, the addition of 0.5% of composition A to the keratinocyte culture medium has the effect of increasing cytokeratin synthesis. Composition A restores the activity of keratinocytes from old skin and also the secretion of cytokeratin by these keratinocytes (action on keratinocytes subject to estradiol withdrawal; see FIGS. 6, 7 and 8, 9).

In addition, calcium-dependent PTHrp synthesis by the keratinocytes is stimulated in the presence of composition A. The PTHrp, synthesized mainly by the keratinocytes, is particularly active in the presence of the calcium ion provided by composition A and acts synergistically with the cytokines of the complete organic matrix of the mother-of-pearl present in composition A.

Decorin, a major adhesion protein in skin regeneration, is also stimulated in the presence of composition A.

Cadherins, calcium-dependent adhesion proteins, are also largely responsible for cohesion. They are stimulated in the presence of composition A.

1.2) Activity of Composition a on Fibroblasts, Elastin Synthesis 1.2.1) Elastin Synthesis by Human Fibroblasts Cultured in the Presence of Composition A The method used is the same as that described in paragraph 1.1.1) above for the study on keratinocytes.

Figure 10:
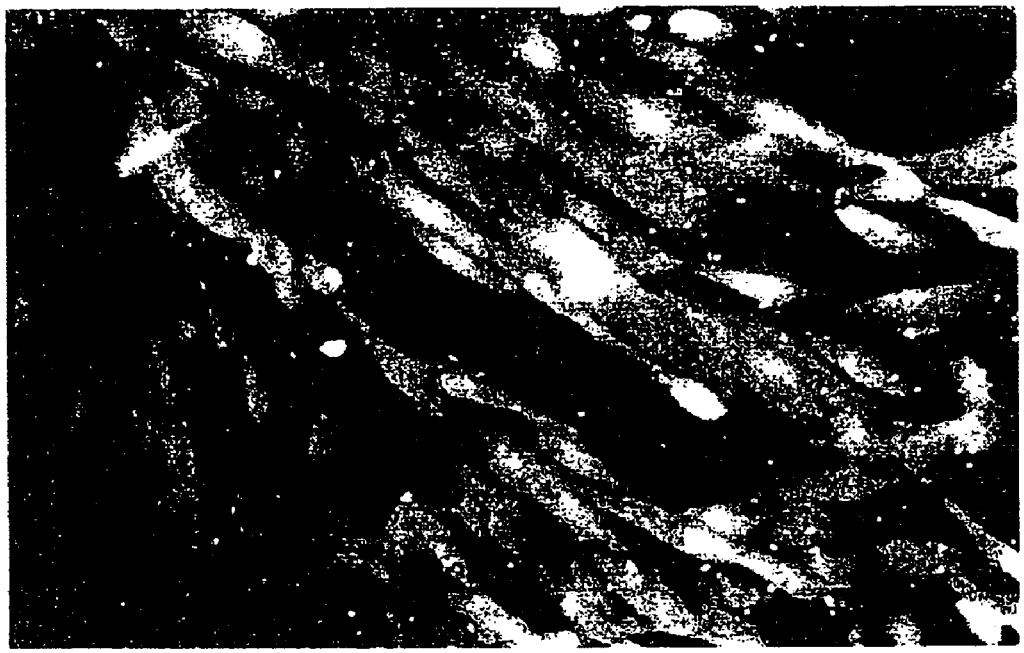
FIGS. 10 and 11 are photographs illustrating the effect of the composition prepared according to the invention on elastin synthesis by human fibroblasts.
Figure 10:
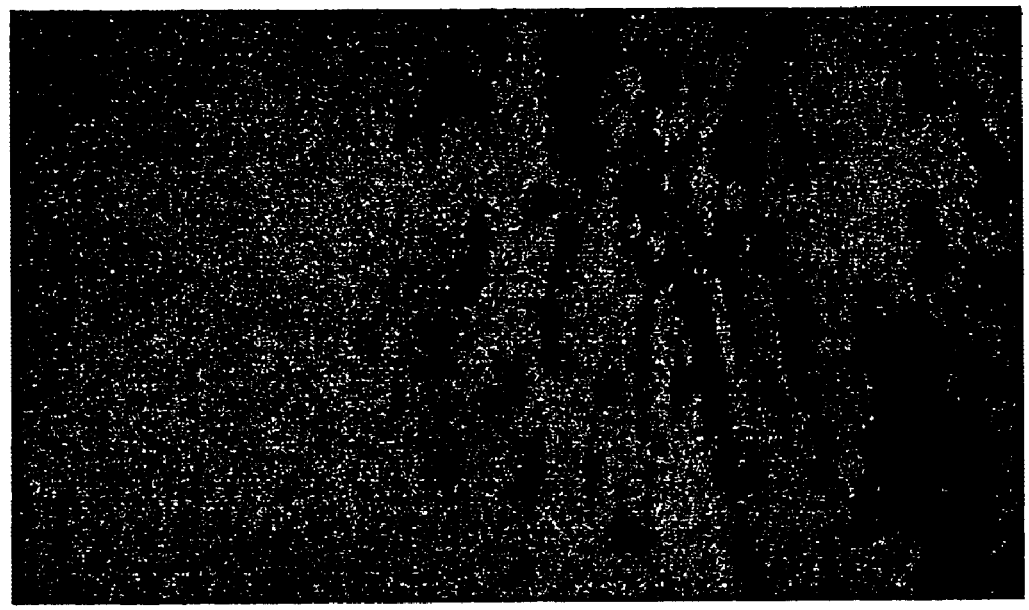
Figure 11:
Figure 11:

As emerges from FIGS. 10 and 11, composition A at a concentration of 1% strongly stimulates elastin synthesis by human fibroblasts.

1.2.2) Comparison of the Effect of Estrogens and of Biocrystal maxima m. on Human Fibroblasts in Culture (FIGS. 12, 13, 14 and 15).

Relatively inactive mature fibroblasts are very elongated and flat in shape and have dense nuclei. Active fibroblasts have nuclei which are large in size and rounded, with voluminous nucleoli, reflecting the active process of synthesis. The "active fibroblast" type is observed in the cultures of skin explants taken from a 50-year-old woman undergoing hormone replacement therapy.

Estrogen deprivation in the culture medium causes drastic inactivation of the cells. They are no longer adherent nor confluent, and some exhibit the beginning of pyknosis.

Figure 12:
FIGS. 12 and 13 are photographs illustrating the effect of estrogens on human fibroblasts.
Figure 14:
FIGS. 14 and 15 are photographs illustrating the effect of the composition prepared according to the invention on human fibroblasts subjected to estradiol withdrawal.

FIGS. 12 and 14 illustrate the effect of composition A on human fibroblasts from explants from 50-year-old menopausal (therefore with decreased estrogen secretion) women undergoing replacement therapy.

Figure 13:
Figure 15:

FIGS. 13 and 15 illustrate the effect of composition A on human fibroblasts subjected to estradiol withdrawal, from explants from 50-year-old menopausal women undergoing replacement therapy.

As emerges from these FIGS. 12 to 15, composition A, added to the culture medium at 1%, completely restores the activity of the fibroblasts having been subjected to the withdrawal. The action of composition A is notable: fibroblasts have a well-developed, very clear nucleus with a prominent nucleolus. Their fusiform cell bodies line up in the same direction and are confluent, allowing cellular exchanges. Similar results were obtained when working on cells from explants of young skin.

1.3) Activity of Composition A on Melanocytes: Modification of the Amount of Melamin Taken Up by Keratinocytes Cultured in the Presence of Composition A 1.3.1) Method Melanocytes are the pigmentary cells responsible for melanin synthesis, melanin being the pigment which causes skin color. Melanocytic cells represent approximately 2 to 4% of the total epidermal population. The homogeneous color of the skin is due to distribution of the pigment over the entire surface of the skin by virtue of melanin transfer, in the form of melanosomes, from the secretory cells (melanocytes) to the neighboring keratinocytes which take it up.

The method consists in preparing a keratinocyte/melanocyte coculture and assaying melanin.

Keratinocytes and melanocytes are both cell populations located in the epidermis. They are obtained from a skin sample after removal of the dermis and enzymatic digestion of the epidermis. The epidermal cells thus isolated are counted in a Coulter Counter (Coultronics) and are then cultured in a conventional culture medium of the medical Dulbeco type (eagle medium) supplemented with glutamine, streptomycin/penicillin and 10 of fetal calf serum. The percentages are adjusted as a function of the results obtained. This medium allows survival of melanocytes and keratinocytes.

After incubation for 4 days in the presence of composition A, the cells are digested with an NaOH/DMSO mixture and the supernatant is then recovered after centrifugation. Reading is performed at 470 nm.

1.3.2) Results

Figure 16:
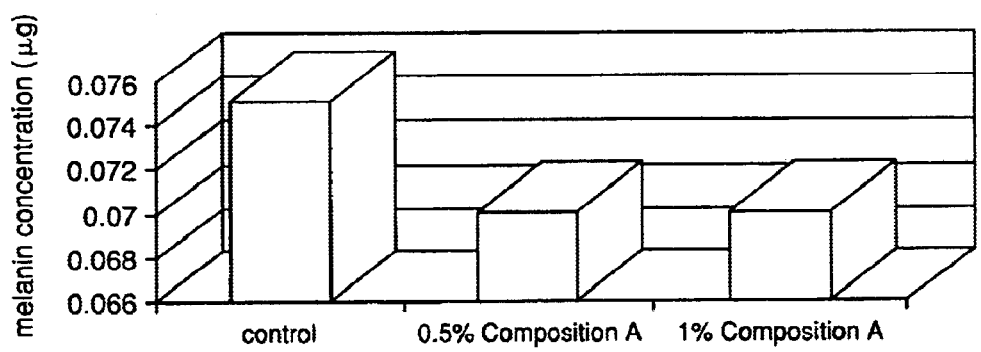
FIG. 16 is a histogram illustrating the effect of the composition prepared according to the invention on melanocytes, through the modification of the amount of melanin taken up by keratinocytes cultured in the presence of the composition.

The results are given in table 2 below and represented by the histogram in FIG. 16.

TABLE 2

μg of melanin taken up by keratinocytes

|  | Sample 1 | Sample 2 | Sample 3 | Mean | Standard deviation |
|---|---|---|---|---|---|
| Control | 0.150 | 0.149 | 0.148 | 0.149 | 0.001 |
| Composition A (0.5%) | 0.150 | 0.132 | 0.140 | 0.141 | 0.009 |
| Composition A (1%) | 0.139 | 0.137 | 0.143 | 0.140 | 0.003 |

Figure 17:
FIGS. 17 and 18 are photographs illustrating the effect of the composition prepared according to the invention on the amount of melanin taken up by cultured human keratinocytes.
Figure 18:
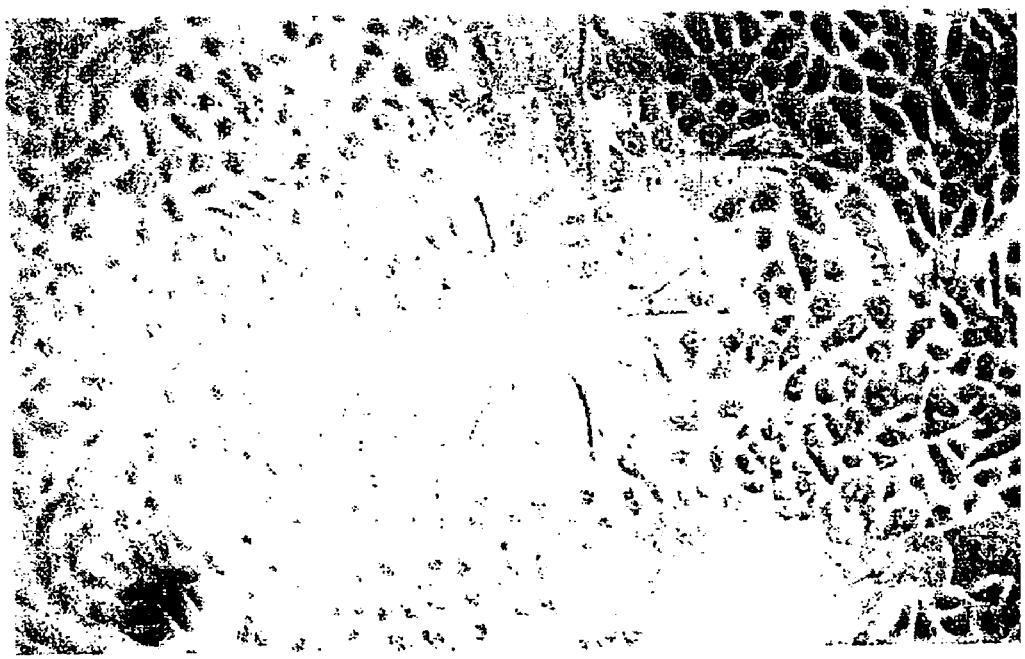

The presence of 1 of composition A causes a significant change in distribution of the melanin taken up by the keratinocytes, avoiding localized concentrations (see FIGS. 17 and 18).

1.4) Immunocytochemical Demonstration of the Stimulation of Keratinocytes and of Fibroblasts by Composition A 1.4.1) Method This is a rapid semiquantitative technique which makes it possible to assess the level of each of the proteins (cytokeratin and elastin) present in the cell cytoplasm. $4 \times 10^4$ cells are seeded per 0.9 cm$^2$ chamber (8-chamber slide, NUNC) and cultured overnight. After rinsing with HBSS buffer, the medium containing 1% of composition A or the control medium (containing 0% of composition A) is added (450 μl per chamber). The cultures are incubated for 48 hours. After the supernatants have been removed and the cultures rinsed, the cells are fixed with paraformaldehyde for 30 minutes at 4° C. and then rinsed with PBS buffer. 200 μl of anti-cytokeratin and/or anti-elastin antibodies are added. The incubation lasts 30 minutes at room temperature. The supernatants are then removed and the cells are rinsed with PBS. 200 μl of the second antibody conjugated to fluorescein are added. After incubation for 30 minutes, the supernatants are removed and the cells are rinsed with PBS. The slides are then mounted, followed by examination under an inverted fluorescence microscope. The amounts of elastin or of cytokeratin synthesized by the cells are proportional to the strength of the fluorescence.

1.4.2) Results

The addition of 1% of composition A to the keratinocyte culture medium has the effect of increasing cytokeratin synthesis by the keratinocyte cells of the epidermis. This stimulation is observed considerably from 0.5% of composition A.

When the fibroblasts are incubated in vitro in the presence of composition A (at 1%) a very noticeable increase in the strength of the fluorescence is observed, after 48 hours, thus reflecting stimulation of elastin synthesis by the fibroblasts of the dermis.

1.5) Anti-Inflammatory Activity of Composition A: Assaying of Interleukin 1 (Il-1) Secreted by HL 60 Promyelocytic Cells Treated with Composition A During an inflammatory process, migration of a large number of inflammatory cells from the peripheral blood to the sizes of inflammation is first observed, followed by considerable secretion at these sites of certain cytokines and in particular of IL-1. The latter is considered to have a major role.

In this study, IL-1 secretion is measured using a cell line, HL-60, in the presence of composition A.

The production of IL-1 is amplified by adding phytohemaglutinin (PHA), which is a powerful stimulant of IL-1 secretion, to the culture medium. The IL-1 is quantified via the conventional technique of immunoassay by ELISA using a specific antibody directed against human IL-1.

1.5.2) Results

Figure 19:
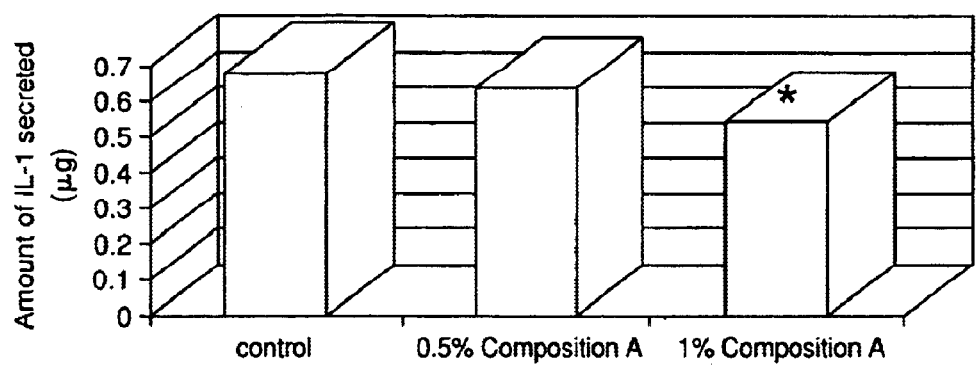
FIG. 19 is a histogram illustrating the effect of the composition prepared according to the invention on interleukin 1 (IL-1) secretion by HL 60 promyelocytic cells.

The results are given in table 3 below and represented by the histogram in FIG. 19.

TABLE 3 demonstration of the effect of composition A on the production of interleukin 1 (IL-1, in picograms) secreted by the promyelocytic cells

|  | Sample 1 | Sample 2 | Sample 3 | Mean | Standard deviation |
|---|---|---|---|---|---|
| Control | 0.703 | 0.685 | 0.654 | 0.681 | 0.025 |
| Composition A (1%) | 0.689 | 0.664 | 0.570 | 0.641 | 0.063 |
| Composition A (0.5%) | 0.494 | 0.615 | 0.527 | 0.545 | 0.063 |

In the presence of 1% of composition A, a significant decrease in IL-1 synthesis is therefore observed, thus reflecting a very notable anti-inflammatory effect of composition A. This in vitro effect was also observed when implantation was performed in rats in vivo.

1.6) Toxicity Test. Demonstration of the Noncytotoxicity of Composition A: MTT Test of Mitochondrial Activity 1.6.1) Method This a colorimetric test based on reduction of a tetrazolium salt (MTT), by the mitochondrial NADPH reductase of live cells, to a blue-purple formazan product.

$2 \times 10^4$ cells, in 200 μl of culture medium, are seeded into each well (96-well plate, NUNC), and then incubated overnight in order to allow them to adhere properly to the plastic. After rinsing the cells with serum-free medium, the various concentrations contained in the culture medium (1%, 0.5% and 0.1% of composition A) or the control medium (0% of composition A), are added at 200 μl/well.

After incubation for 48 hours, the supernatants are removed and the cells are rinsed with HBSS buffer. 100 μl of culture medium containing 20% of a solution of MTT (3-[4,5-dimethylthiazol-2-yl]-2,5-diphenyl-tetrazolium bromide; "Thiazolyl Blue") are added to each well. The reaction takes place for 2 hours in an incubator at 37° C. at 5% $CO_2$.

100 μl of 0.04 N HCl in isopropanol are added to allow better solubilization of the formazan crystals, and then the colored reaction is read at a wavelength of 570 nm using a microplate reader. The values are also expressed as optical density.

1.6.2) Results

The results are given in table 4 and represented by the histogram in FIG. 20.

TABLE 4

| | optical density measured | | | | | | | |
|---|---|---|---|---|---|---|---|---|
| | Sample 1 | Sample 2 | Sample 3 | Sample 4 | Sample 5 | Sample 6 | Mean | Standard deviation |
| Control | 0.455 | 0.466 | 0.449 | 0.449 | 0.47 | 0.472 | 0.460 | 0.01 |
| Composition A (1%) | 0.732 | 0.796 | 0.771 | 0.785 | 0.808 | 0.768 | 0.777 | 0.027 |
| Composition A (0.5%) | 0.669 | 0.675 | 0.709 | 0.7 | 0.598 | 0.694 | 0.691 | 0.016 |
| Composition A (0.1%) | 0.643 | 0.648 | 0.617 | 0.624 | 0.621 | 0.628 | 0.630 | 0.013 |

The presence of composition A in the culture medium therefore leads to a considerable increase in the cellular mitochondrial activity. This stimulation of the enzymatic activity is dose-dependent: the higher the concentration of composition A, the higher the activity. However, whatever the content of composition A in the medium, the mitochondrial activity of the cells is greatly superior to that of the control cells not treated with composition A.

2.7) Conclusions Regarding the Activity of Composition A Evaluated In Vitro

Composition A acts directly on the most superficial layers of the epidermis.

The organic and inorganic components of the extract express themselves at several levels in keratinocyte metabolism by acting on the activity of the cells of the basal layer.

First of all, cell growth, division and differentiation are stimulated and then specific syntheses by the keratinocytes are amplified, in particular syntheses of cytokeratins and the mediators intended for correct functioning of the dermis, such as for example PTHrp, promoting the intercellular communication cascade.

The differentiation sequence for basal keratinocytes which are star-shaped and then granular, is stimulated and controlled without any increase in the number of cells.

The controlled increase in the number of keratinocytes improves the structure of the epidermis and the dermal-epidermal junctions. The restructuring of the epidermis contributes to better protection of the deepest layers.

The improvement in specific syntheses, such as those of the cytokeratins, stabilizes pigment syntheses and ensures a physiological repartition of the melanin within the keratinocytes, resulting in the lack of localized concentrations. The improvement in the protection of the skin occurs without inducing any abnormal thickening of the skin, while at the same time deepening the sheets of cells layered on the dermal-epidermal junction.

Substances which contribute to improving the response of cells to attack and to inflammation, and also the communication factors which allow physiological exchanges between the epidermis and dermis, are found among the set of mediators secreted by the keratinocytes. The cellular renewal of the epidermis, which is 4 to 6 weeks, is maintained at its physiological rhythm.

Amplification of mediator synthesis increases the recruitment of an entire set of cells, and the decorin provided by composition A at the epidermal level is included among these mediators.

2.7.1) At the Epidermal Level

By activating PTHrp synthesis, composition A acts on the growth and differentiation of keratinocytes. This effect is calcium-dependent, hence the advantage of the presence of the ionized calcium in composition A.

The induction of cell division and of the mitotic index in the germinal layer results in a real restructuring of the epidermis, which becomes more resistant and deeper, and interacts continually with the dermis, which it protects against dehydration.

2.7.2) At the Dermal Level

The stimulation cascade produced by the local mediators released in the epidermis causes the synthesis of a very abundant extracellular matrix by the fibroblasts. This is very structured. It is in particular composed of proteoglycans, of collagen and of adhesion proteins, in particular of decorin, an adhesion protein which plays a major role in the phenomena of restructuring of the skin (or skin tissue regeneration). It traps cytokines and other growth factors. These observations were also noted in viva in rats.

Moreover, the enrichment in elastin under the effect of composition A, the fibers of which exhibit better orientation in the connective layer, allow skin tissues to keep their suppleness and their shape during the physiological degradations caused either by deficiencies and age, or by attacks, in particular stretching.

Turgescent fibroblasts are recruited to the precursor stem cells in sufficient number for the effect due to their action and presence to be long-lasting. This effect is maintained by an increased microvascularization.

The skin is more elastic and firmer. It is resistant. Its components are renewed at a sustained rhythm.

The action of composition A on the various cell types of the skin is one of repair and regulation of the physiological balance between the various constituents. In addition, it has the advantage of being totally innocuous and that of having an anti-inflammatory, and therefore soothing, effect.

EXAMPLE 3

Moisturizing Cream

| Moisturizing cream | |
|---|---|
| INCI name | 100 kg |
| PEG-100 STEARATE GLYCERYL STEARATE | 1.000 |
| LIQUID PARAFFIN | 3.500 |
| LANOLIN | 1.700 |
| MYRISTYL ETHOXYMYRISTATE | 4.000 |
| PLANT OILS | 4.000 |
| CETYL ALCOHOL | 2.500 |
| TRIETHANOLAMINE | 0.200 |
| ANTIOXIDANT | 0.030 |
| PROPYL PARABEN | 0.300 |
| CARBOMERS | 0.250 |
| DISODIUM EDTA | 0.400 |
| PROPYLENE GLYCOL | 2.000 |
| PRESERVING AGENT | 0.600 |
| POLYACRYLAMIDE/C13–14 ISOPARAFFIN/LAURETH-7 | 1.000 |
| Composition A | 2.500 |
| FRAGRANCE | TRACE |
| WATER | QS for 100 |

What is claimed is:

1. A method for preparing a composition, comprising the steps of:
   a) reducing mother-of-pearl to a powder with to a particle size of between approximately 1 µm and approximately 300 µm;
   b) bringing mother-of-pearl powder thus obtained into contact with an extracting agent chosen from an aqueous-glycolic solution of at least one collagen, an aqueous glycolic solution of at least one proteoglycan, or an aqueous glycolic solution of a mixture of at least one collagen and at least one proteoglycan, to obtain an extraction mixture; and
   c) recovering the extraction mixture formed as a result of the bringing into contact.

2. The method as claimed in claim 1, wherein the mother-of-pearl is reduced to a powder with a particle size of between approximately 50 µm and approximately 100 µm.

3. The method as claimed in claim 1, wherein the mother-of-pearl is reduced to a powder with a particle size of between approximately 15 µm and approximately 50 µm.

4. The method as claimed in claim 1, wherein the aqueous-glycolic solution of the extracting agent has a water:glycol weight ratio of approximately 1:100.

5. The method as claimed in claim 1; wherein the collagen is a marine collagen.

6. The method as claimed in claim 1, wherein the collagen concentration is between approximately 0.0001% and approximately 50% by weight, relative to the total weight of the extracting agent.

7. The method as claimed in claim 1, wherein the extracting agent is an aqueous-glycolic solution of at least one proteoglycan.

8. The method as claimed in claim 7, wherein the proteoglycan is chosen from the group consisting of hyaluronic acid, chondroitin sulfate, dermatan sulfate, heparan sulfate, keratan sulfate and mixtures thereof.

9. The method as claimed in claim 7, wherein the extracting agent is an aqueous-glycolic solution of hyaluronic acid.

10. The method as claimed in claim 7, wherein the proteoglycan concentration is preferably between approximately 0.0001 and approximately 40% by weight, relative to the total weight of the extracting agent.

11. The method as claimed in claim 1, wherein the mother-of-pearl powder is brought into contact with the extracting agent according to step b) by preparing a mixture, including the mother-of-pearl powder and the extracting agent, wherein it comprises, relative to its total weight, approximately 20% to approximately 60% by weight of mother-of-pearl powder obtained in step a) and the remainder as extracting agent.

12. The method as claimed in claim 1, wherein the contact in step b) is brought about, for a given temperature, for a period of time sufficient to produce a substantially complete extraction.

13. The method as claimed in claim 1, wherein at the end of step b), the extraction mixture, formed as a result of the bringing into contact, is recovered and a liquid phase of the composition is separated from a solid phase.

14. A composition obtained using the method as claimed in claim 1.

15. The composition as claimed in claim 14, in the form of an aqueous-glycolic suspensions, comprising:
   aragonite ($CaCO_3$);
   trace elements chosen from the group consisting of sodium, magnesium, lanthanum, zinc, bromine, cesium, iron, manganese, chlorine, copper, potassium, calcium, strontium, sulfur and mixtures thereof;
   fibrous proteins from mother-of-pearl;
   nonfibrous proteins from mother-of-pearl; and
   at least one collagen not derived from mother of-pearl and/or at least one proteoglycan not derived from mother-of-pearl.

16. The composition as claimed in claim 14, comprising at least one marine collagen not derived from mother-of-pearl and at least one proteoglycan not derived from mother-of-pearl chosen from the group consisting of hyaluronic acid, chondroitin sulfate, dermatan sulfate, heparan sulfate, keratan sulfate and mixtures thereof.

17. A pharmaceutical composition, comprising the composition as claimed in claim 14, as an active principle, and at least one pharmaceutically acceptable excipient.

18. The pharmaceutical composition as claimed in claim 17, wherein the pharmaceutically acceptable excipient is an excipient suitable for dermatological application.

19. A therapeutic method-intended for the treatment of tissue regeneration disorders of skin and/or superficial body growths, comprising a step of applying to the skin and/or superficial body growths a composition as claimed in claim 14.

20. A therapeutic method for treatment of disorders of skin and/or superficial body growths related to aging comprising a step of applying to skin and/or to superficial body growths a composition as claimed in any one of claims 14 to 16.

21. A therapeutic method for treatment of inflammatory skin manifestations comprising a step of applying to skin and/or superficial body growths a composition as claimed in any one of claims 14 to 16.

22. A cosmetic composition, comprising the composition as claimed in claim 14, as a cosmetically active principle, and a cosmetically acceptable excipient.

23. A cosmetic method-intended-for-cosmetic-treatment for tissue regeneration of skin and/or superficial body growths comprising a step of applying to skin and/or to superficial body growths a composition as claimed in claim 14.

24. A cosmetic method for cosmetic treatment of modifications related to aging of skin and/or superficial body growths comprising a step of applying to skin and/or to superficial body growths a composition as claimed in claim 14.

25. A method for preparing a composition, comprising the steps of:

a) reducing mother-of-pearl to a powder to a particle size of between approximately 1 $\mu$m and approximately 300 $\mu$m;

b) bringing mother-of-pearl powder thus obtained into contact with an extracting agent in the form of an aqueous-glycolic solution to obtain an extraction mixture of at least on of a collagen and a proteoglycan; and c) recovering the extraction mixture formed as a result of the bringing into contact.

26. The method as claimed in claim 1, wherein the aqueous-glycolic solution extracting agent has a water:glycol weight ratio of approximately 100:1.

* * * * *

UNITED STATES PATENT AND TRADEMARK OFFICE
CERTIFICATE OF CORRECTION

PATENT NO. : 6,936,280 B1 Page 1 of 1
APPLICATION NO. : 10/089982
DATED : August 30, 2005
INVENTOR(S) : Lopez et al.

It is certified that error appears in the above-identified patent and that said Letters Patent is hereby corrected as shown below:

COL. 19, LN 27
In Claim #1, Line #3, please delete "with".

COL. 20, LN 49
In Claim #19, Line #1, please delete "intended".

COL. 20, LN 49
In Claim #19, Line #1, please delete "the".

COL. 21, LN 1,
In Claim #23, Line #1, please delete "intended for cosmetic treatment".

COL. 21, LN 7,
In Claim #25, Line #9, please delete "on" and insert -- one --.

COL. 21, LN 10,
In Claim #26, Line #2, after "solution" please insert -- of the --.

Figure 8:
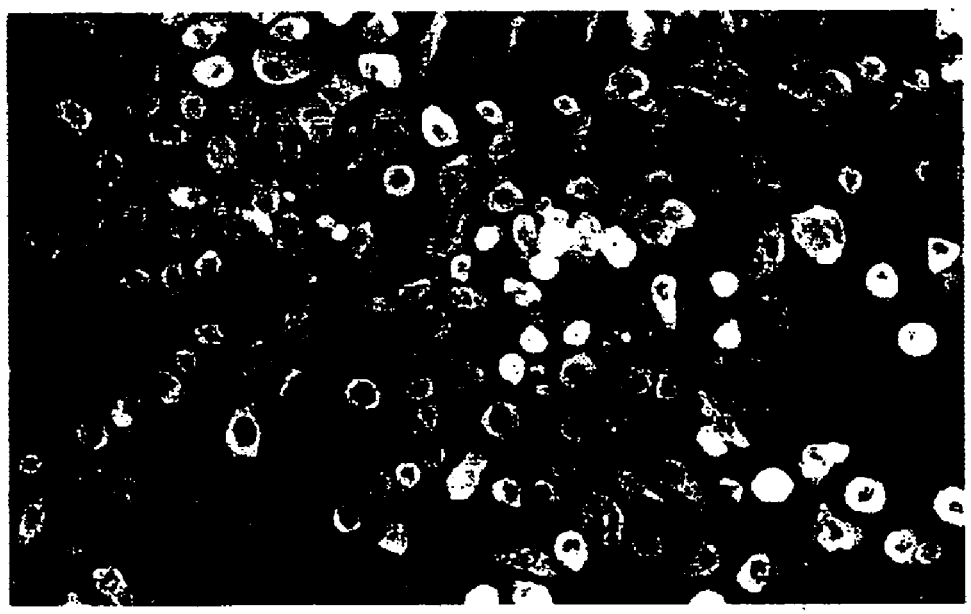
FIGS. 8 and 9 are photographs illustrating the effect of the composition prepared according to the invention con cytokeratin synthesis by human keratinocytes in culture subjected to estradiol withdrawal.
Figure 9:
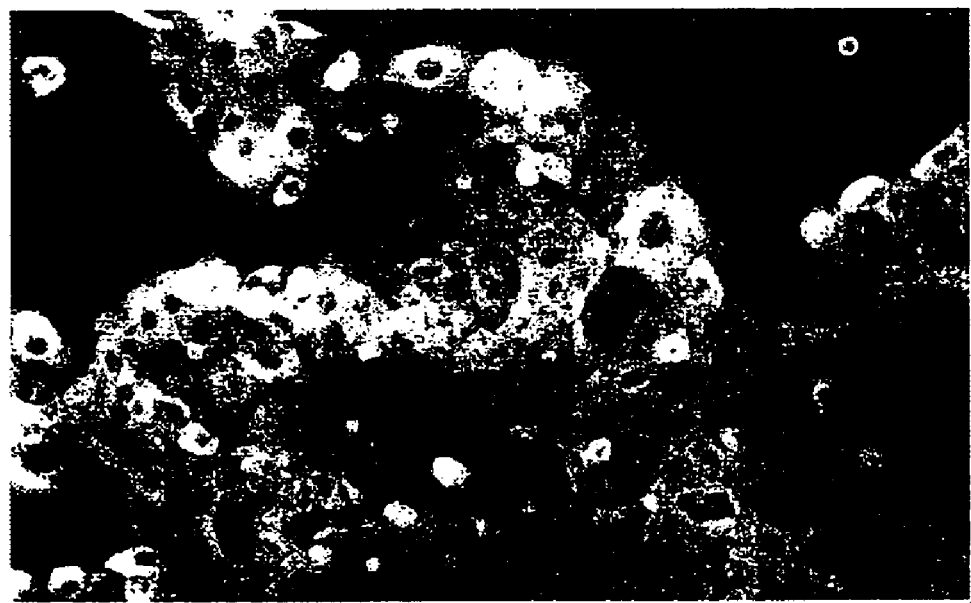

In the Brief Description of the Drawings, FIGS. 8 and 9, Line #2, please delete "con" and insert -- on --.

Signed and Sealed this

Twenty-third Day of October, 2007

JON W. DUDAS
*Director of the United States Patent and Trademark Office*